(12) United States Patent
Stewart et al.

(10) Patent No.: US 7,872,318 B2
(45) Date of Patent: Jan. 18, 2011

(54) SENSING DEVICES AND METHODS FOR FORMING THE SAME

(75) Inventors: Duncan R. Stewart, Palo Alto, CA (US); Amir A. Yasseri, Mountain View, CA (US); R. Stanley Williams, Palo Alto, CA (US); Theodore I. Kamins, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 57 days.

(21) Appl. No.: 11/584,103

(22) Filed: Oct. 20, 2006

(65) Prior Publication Data

US 2008/0079104 A1 Apr. 3, 2008

Related U.S. Application Data

(63) Continuation-in-part of application No. 11/537,589, filed on Sep. 29, 2006, now Pat. No. 7,638,431.

(51) Int. Cl.
*H01L 27/14* (2006.01)
(52) U.S. Cl. ............... 257/414; 257/433; 257/E51.011; 257/E21.576; 257/E21.581
(58) Field of Classification Search .................. 257/13, 257/433, 414; 438/64, 69; 977/762, 949
See application file for complete search history.

(56) References Cited

U.S. PATENT DOCUMENTS

| | | | | |
|---|---|---|---|---|
| 6,297,063 | B1* | 10/2001 | Brown et al. | 438/2 |
| 7,087,920 | B1 | 8/2006 | Kamins | |
| 2003/0145779 | A1* | 8/2003 | Alivisatos et al. | 117/2 |
| 2004/0175844 | A1* | 9/2004 | Yang et al. | 438/2 |
| 2005/0133476 | A1* | 6/2005 | Islam et al. | 216/2 |
| 2006/0038990 | A1* | 2/2006 | Habib et al. | 356/301 |
| 2006/0055920 | A1* | 3/2006 | Wang et al. | 356/301 |
| 2006/0097389 | A1* | 5/2006 | Islam et al. | 257/734 |

OTHER PUBLICATIONS

Sun et al., "Silicon Nanowires Wrapped with Au Film" J. Phys. Chem. B 2002, 106, 6980-6984.*
X. H. Sun et al., "Zero-Dimensional Nanodots on One-Dimensional Nanowires: Reductive Deposition of Metal Nanoparticles on Silicon Nanowires", Jun. 2004, pp. 199-224, vol. 15, No. 2.*
Yasseri, A. et al., "Growth and use of metal nanocrystal assemblies on high-density silicon nanowires formed by chemical vapor deposition," Appl Phys A, 82, 2006, pp. 659-664.

\* cited by examiner

*Primary Examiner*—Ahmed Sefer (57) ABSTRACT

A sensing device includes an optical cavity having two substantially opposed reflective surfaces. At least one nanowire is operatively disposed in the optical cavity. A plurality of metal nanoparticles is established on the at least one nanowire.

24 Claims, 5 Drawing Sheets

SENSING DEVICES AND METHODS FOR FORMING THE SAME

CROSS REFERENCE TO RELATED APPLICATIONS

This application is a continuation-in-part of U.S. patent application Ser. No. 11/537,589, filed on Sep. 29, 2006 now U.S. Pat. No. 7,638,431, entitled "Composite Nanostructure Apparatus and Method" by inventors Amir Yasseri, Theodore I. Kamins and Shashank Sharma, which application is incorporated by reference herein in its entirety.

BACKGROUND

The present disclosure relates generally to sensing devices and to methods for forming the same.

Since the inception of semiconductor technology, a consistent trend has been toward the development of smaller device dimensions and higher device densities. As a result, nanotechnology has seen explosive growth and generated considerable interest. Nanotechnology is centered on the fabrication and application of nano-scale structures, or structures having dimensions that are often 5 to 100 times smaller than conventional semiconductor structures. Nanowires are included in the category of nano-scale structures.

Nanowires are wire-like structures having at least one linear dimension ranging from about 3 nm to about 200 nm. Nanowires are suitable for use in a variety of applications, including functioning as conventional wires for interconnection applications or as semiconductor devices. Nanowires are also the building blocks of many potential nano-scale devices, such as nano-scale field effect transistors (FETs), p-n diodes, light emitting diodes (LEDs) and nanowire-based sensors, to name a few. A primary drawback of conventional sensing techniques is a small area of the sensing surface, and, thus, limited ability to interact with a sample.

BRIEF DESCRIPTION OF THE DRAWINGS

Features and advantages of the present disclosure will become apparent by reference to the following detailed description and drawings, in which like reference numerals correspond to similar, though not necessarily identical components. For the sake of brevity, reference numerals or features having a previously described function may not necessarily be described in connection with other drawings in which they appear.

DETAILED DESCRIPTION

Embodiments of the sensing device and system disclosed herein advantageously have enhanced optical intensity and enhanced sensitivity. Without being bound to any theory, it is believed that this may be due, at least in part, to the addition of nanowires having metal nanoparticles thereon to an optical cavity having two opposed reflective surfaces. The optical cavity of the sensing device may advantageously enhance the light and/or signal that is/are produced during spectroscopic analysis. Moreover, it has been found that conventional sensing techniques may be augmented with more effective techniques that are especially advantageous when nanowires are used. For example, surface-sensitive techniques, such as surface-enhanced Raman spectroscopy (SERS) may be dramatically enhanced by providing a very large area of nano-structured surface to interact with the sample. Furthermore, the optical cavity may be designed to have a desirable quality ("Q") factor, and may be designed for a wavelength of interest.

Figure 1:
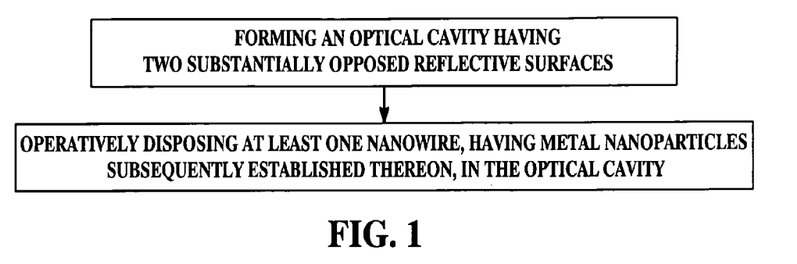
FIG. 1 depicts an embodiment of a method for forming a sensing device.

Referring now to FIG. 1, a general embodiment of a method for forming a sensing device is depicted. The method includes forming an optical cavity having at least two substantially opposed reflective surfaces; and operatively disposing at least one nanowire (on which metal nanoparticles are subsequently established) in the optical cavity. It is to be understood that embodiments of the method shown in FIG. 1 are described in further detail in reference to the other figures hereinbelow.

Methods for forming nanowires having metal nanoparticles subsequently established thereon (also known as "decorated" nanowires) are described in the parent pending U.S. Patent Application referenced above, filed on Sep. 29, 2006; which application generally describes these decorated nanowires established on a surface.

Figure 2A:
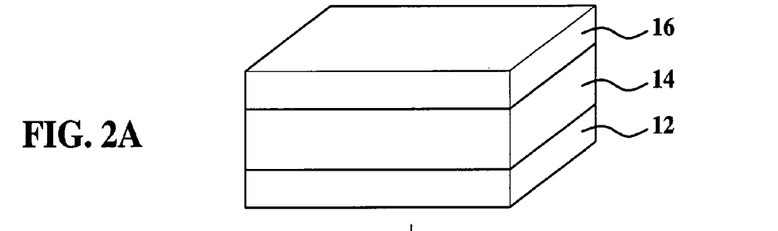
FIGS. 2A through 2C depict semi-schematic perspective views of an embodiment of the method for forming an embodiment of the sensing device.
Figures 2B, 2C:
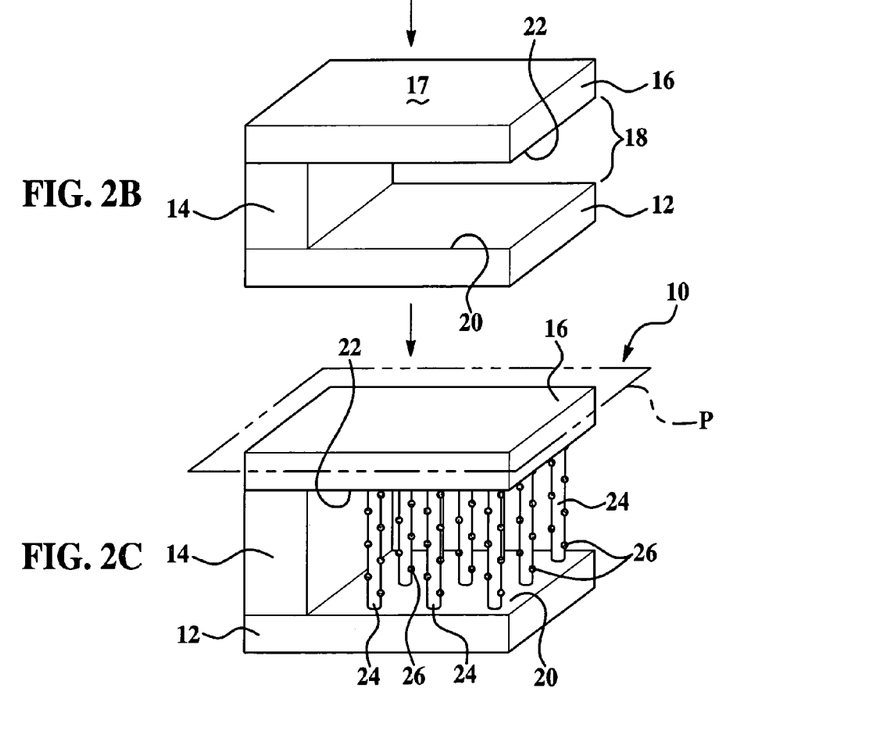

FIGS. 2A, 2B and 2C together depict an embodiment of the method for forming an embodiment of the sensing device 10. Very generally, FIG. 2A depicts a substrate 12 having a spacer layer 14 thereon, and a second layer 16 established on spacer layer 14. FIG. 2B depicts the removal of a portion of the spacer layer 14 to form the optical cavity 18 in an area between the substrate 12 and second layer 16. As shown in FIG. 2B, the optical cavity 18 has two opposed reflective surfaces 20, 22. FIG. 2C depicts the formation of nanowires 24, with nanoparticles 26 subsequently established thereon. It is to be understood that nanoparticles 26 may be formed from any suitable materials, including but not limited to gold, silver, copper, platinum, palladium, alloys thereof, and combinations thereof. It is to be further understood that nanoparticles 26 may be bi-material nanoparticles. Some examples of bi-material nanoparticles 26 include core-shell type structures. In one embodiment, the core and shell of such a structure may be formed from different metallic elements or alloys, some non-limiting examples of which are listed immediately above. In another embodiment, the core of a core-shell structure may be formed from a metallic element or alloy, and the shell may be a dielectric, including, for example, silicon oxide, silicon nitride, metal oxides, glass and/or the like.

Referring more specifically to FIG. 2A, the substrate 12 and/or second layer 16 may be formed of a reflective material or of a stack of materials (the individual layers of which are not shown) having at least one reflective material therein to form reflective surfaces 20, 22, or having layers with varying refractive indices. In any of these embodiments, the reflective surfaces 20, 22 (shown in FIG. 2B) are formed integrally with the respective substrate 12 and second layer 16.

In an embodiment, second layer 16 generally acts as a partially transparent mirror. Second layer 16 may be configured with a reflective top surface 17, and/or a reflective underside surface 22, or a distributed Bragg reflector 50 (see FIG. 2E) formed from any desired number of layers, e.g., layers 40, 42, 44, 46, built within the layer 16. As defined herein, "reflective" for use within optical cavity 18 (or within optical cavity 18', described further below) generally means R~0.9 (cavity Q~10, low) to R~0.999999 (Q~$10^6$, very high), or in some cases, even higher.

When a reflective material is selected as the substrate 12 and/or second layer 16, it is to be understood that any reflective material may be suitable that is capable of serving as a substrate or layer on which nanowires 24 can be grown or attach. Non-limiting examples of such materials include silicon, germanium, gallium arsenide, silicon germanium, indium phosphide, gallium nitride, aluminum arsenide, or the like, or combinations thereof. These materials are available in the form of wafers or other like substrate forms, and/or may be established as layers on some other substrate.

When a stack of materials is selected as the substrate 12, it is to be understood that the stack is generally formed prior to establishing the spacer layer 14 thereon. Alternately or additionally, the stack of materials may be deposited, e.g., via conformal deposition, after etching cavity 18 so that the stack is formed on second layer 16, as well as on substrate 12. Such deposition may be desirable if the stack of materials is very thin (as in the case of a Bragg reflector, which generally may be about 2-10 wavelengths or more thick), and thus would benefit from mechanical support provided by, e.g., a substrate. When the stack of materials is placed on the second layer 16 before etching the cavity 18, it is to be understood that the stack and second layer 16 may be formed on the spacer layer 14, or may be formed separately and then established as a single unit on the spacer layer 14. The stack(s) may include any number of materials, as long as one of the materials has a refractive index different from the other materials. The materials are chosen to optimize the reflectivity of the total stack of materials. In an embodiment, the stack is a Bragg reflector, where the constructive interference from all the layers with varying (generally alternating) refractive indices yields high mirror reflectivity. Suitable techniques for forming the stack(s) include, but are not limited to electron-beam evaporation, sputtering, electro-deposition, electroless deposition, and atomic-layer deposition (ALD).

Generally, the materials within the stack(s) and the thickness of each layer in the stack may be tuned or selected to achieve maximum reflectivity at a desirable wavelength. Furthermore, if nanowires 24 are to be grown from the stack of materials forming the substrate 12 and/or second layer 16, it is to be understood that the stack and/or the nanowire growth process may be designed so that none of the layers in the stack subtantially interfere with nanowire growth.

FIGS. 2A and 2B together depict the presence and partial removal of the spacer layer 14. It is desirable that the substrates 12, 16 remain substantially unaltered after removal of the portion of the spacer layer 14. As such, the spacer layer 14 may be any material that exhibits different etch characteristics than those of the selected substrate 12 and second layer 16. For example, spacer layer 14 may have a different etch rate than the etch rate of the selected substrate 12 and second layer 16, and/or spacer layer 14 may be etched by a material(s) to which selected substrates 12, 16 are resistant. As a non-limiting example, if silicon is used as substrate 12 and layer 16, silicon dioxide may be incorporated as the spacer layer 14. As another non-limiting example, if gallium arsenide is used as the substrate 12 and layer 16 materials, aluminum gallium arsenide may be used as the spacer layer 14. Removal of the spacer layer 14 may be accomplished by wet chemical etching, isotropic plasma etching, or combinations thereof. Generally, reactive ion etching is not suitable for removal of the spacer layer 14, in part, because a lateral undercut is generally desirable.

The removal of the portion of the spacer layer 14 exposes a portion of each of the substrate 12 and layer 16, and forms a cavity defined by the substrate 12, layer 16 and the remaining portion of the spacer layer 14. In an embodiment in which the exposed substrate 12 and layer 16 materials are also desirable reflective surfaces 20, 22, the removal process completes the formation of the optical cavity 18.

In another embodiment, in which one or both of the exposed substrate 12 and layer 16 materials do not form desirable reflective surfaces 20, 22 (e.g., a higher or different reflectivity is desirable), another layer of reflective material may be established on one or both of the exposed substrate 12 and layer 16 to form surface(s) 20, 22. As such, it is to be understood that it may be desirable to establish the additional layer on one or both of substrate 12 and layer 16 to form reflective surfaces 20, 22, respectively. In this embodiment, the addition of the reflective material completes the formation of the optical cavity 18. Further, it is to be understood that the additional layer of reflective material is selected so as not to inhibit the growth or attachment of nanowires 24 to or from the substrate 12 or layer 16. Alternatively, the additional layer(s) may be added after nanowire 24 growth. Any suitable process for establishing the additional reflective layer(s) may be used, including but not limited to growing the nanowires, followed by selective deposition of reflective material (such as a single layer of metal) (e.g., via atomic-layer deposition (ALD), electrochem/electroless plating, and/or the like) onto the surfaces 20, 22. The additional layer(s) may also be established via non-selective deposition processes (i.e., may be established on a portion(s) of the nanowires 24).

Examples of suitable reflective materials for establishing as a layer(s) on surface 20 and/or surface 22 include, but are not limited to Si, Ge, silicon oxides (including SiO, $SiO_x$, $SiO_2$), $TiO_2$, GaAs, AlGaAs (e.g., on a GaAs surface 20, 22), InGaAs (e.g., on a GaAs surface 20, 22), SiGe (on a Si or Ge surface 20, 22), Al, Au, Rh, Ag, Pt, Ni, Cu, or the like, or combinations thereof.

Referring now to the embodiment shown in FIG. 2C, the nanowires 24 may be grown from the substrate 12 to the second layer 16, from the second layer 16 to the substrate 12, and/or from both of substrate 12 and layer 16 toward each other to form a single nanowire(s) 24. In each of these non-limiting examples of growth scenarios, the formed nanowires 24 contact each of the reflective surfaces 20, 22.

Figure 2D:
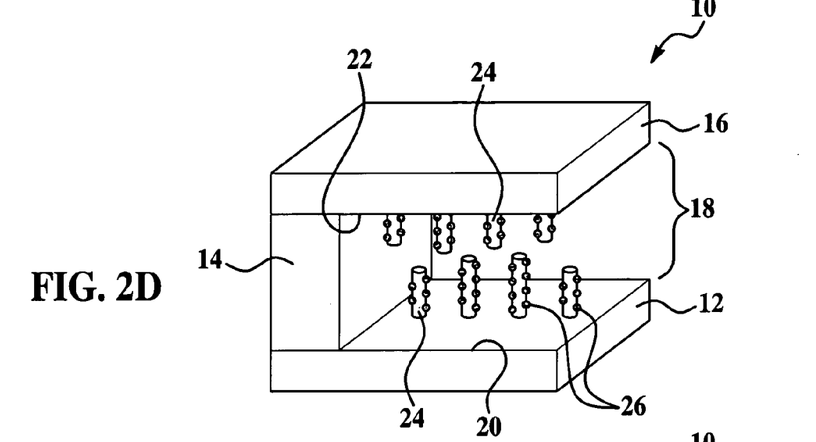
FIG. 2D is a semi-schematic perspective view of an alternate embodiment of the sensing device of FIG. 2C.
Figure 2E:
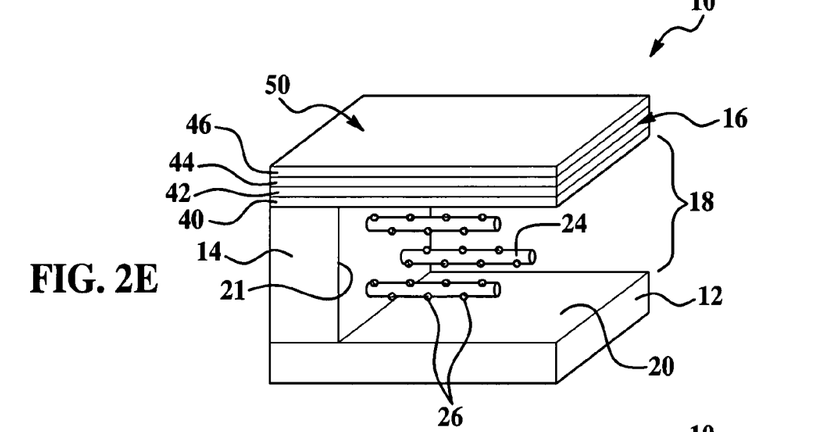
FIG. 2E is a semi-schematic perspective view of yet a further alternate embodiment of the sensing device of FIG. 2C.
Figure 2F:
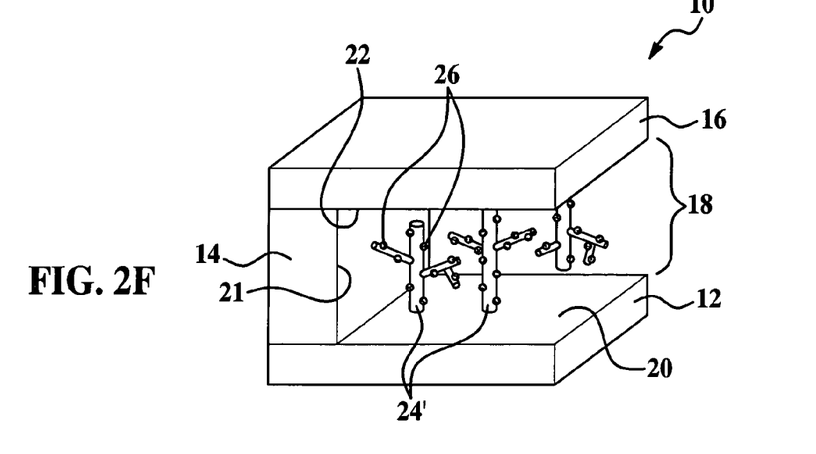
FIG. 2F is a semi-schematic perspective view of still another alternate embodiment of the sensing device of FIG. 2C.

FIGS. 2D through 2F show alternate non-limiting examples of suitable devices 10 according to embodiments of the present disclosure, where nanowires 24 contact a single surface (not necessarily one of the reflective surfaces 20, 22, as demonstrated in FIG. 2E).

FIG. 2D depicts decorated nanowires 24 extending from a respective reflective surface 20, 22. Although nanowires 24 are shown extending from each of surfaces 20, 22, it is to be understood that nanowires 24 could extend solely from surface 20 or solely from surface 22.

FIG. 2E depicts decorated nanowires 24 extending from a surface 21 of spacer layer 14, as well as a Bragg reflector 50 forming layer 16 (it is to be understood that a Bragg reflector 50 may be used as suitable and/or as desired in any of the embodiments described throughout this disclosure). Bragg reflector 50 includes two or more layers having varying refractive indices, for example, layers 40, 42, 44, 46.

FIG. 2F depicts branched decorated nanowires 24' extending from each of the reflective surfaces 20, 22, as well as a branched nanowire 24' contacting each of reflective surfaces 20, 22. The branched nanowires 24' shown at the right and left sides of the figure further include branches extending from branches, and thus may be referred to as "hyper-branched" nanowires.

In an embodiment in which the substrate 12 and layer 16 define the reflective surface(s) 20, 22, "contact" means that the nanowire 24, 24' is grown from or attaches to the reflective surface(s) 20, 22. In an embodiment in which one or more additional layers of reflective material define the reflective surface(s) 20, 22, "contact" means that a portion of the nanowire 24, 24' extends through the reflective surface(s) 20, 22, or that nanowire 24, 24' is attached to the one or more additional layers.

As previously stated, it is to be understood that the reflecting surfaces 20, 22 (whether formed integrally with the substrate 12 or layer 16 or as an additional layer) are selected so that nanowire growth from the substrate 12 and/or layer 16 and/or additional reflective layer(s) is not substantially inhibited.

The substrate 12 and/or layer 16 from which the nanowires 24, 24' are grown may be formed with the surface plane being a (111) crystal lattice plane. Such a substrate 12 or layer 16 is referred to as a (111) oriented Si substrate or layer. In this embodiment, the (111) plane is considered to be horizontally oriented with respect to the Cartesian coordinate system.

In this embodiment, the term "horizontal" generally refers to a direction or a plane that is parallel with plane P shown in FIG. 2C, while the term "vertical" generally refers to a direction or plane that is substantially or approximately perpendicular to the plane P shown in FIG. 2C.

The spacer layer 14 (shown in FIG. 2E) from which the nanowires 24 are grown may be formed with its surface 21 being a (111) crystal lattice plane. In this embodiment, the (111) plane is considered to be vertically oriented with respect to the Cartesian coordinate system.

It is to be understood that the specific use of the terms "horizontal" and "vertical" throughout this disclosure to describe relative characteristics is to facilitate discussion, and is not intended to limit embodiments of the present disclosure.

The (111) surface orientation of enables growth of the nanowires 24, 24'; as such, any suitable method may be used to grow the nanowires 24, 24'. In an embodiment, nanowire 24, 24' growth is accomplished by establishing a catalyst on one or both of the reflective surface(s) 20, 22, or the surface 21, and exposing the catalyst to a precursor gas that initiates growth of the nanowire 24, 24'. The formation of nanowires 24, 24' is further described in U.S. patent application Ser. No. 10/982,051, filed on Nov. 5, 2004 (U.S. Publication No. 2006/0097389, published May 11, 2006), incorporated by reference herein in its entirety.

Non-limiting examples of the types of nanowires 24, 24' that may be formed include silicon nanowires, germanium nanowires, compound semiconductor nanowires (including lattice mis-matched nanowires (e.g., indium phosphide nanowires grown on silicon with a lattice mis-match of about 8%)), or the like, or combinations thereof.

As depicted in FIG. 2C, the nanowires 24 include metal nanoparticles 26 established thereon. As mentioned above, the formation of metal nanoparticles on nanowires is described in further detail in the parent U.S. patent application filed on Sep. 29, 2006. Such formation of metal nanoparticles on nanowires is also described in "Growth and use of metal nanocrystal assemblies on high-density silicon nanowires formed by chemical vapor deposition" by Yasseri et al., published online Dec. 1, 2005, and published in 2006 in volume 82 of *Applied Physics A* at pages 659-664.

In any of the embodiments disclosed herein, while establishing the nanoparticles 26 on nanowires 24, 24' (and 36, 36' shown in FIG. 3A et seq.), one should ensure that the chemicals used in solution and processing do not substantially and/or undesirably degrade the optical properties of reflective surfaces 20, 22.

Figure 3A:
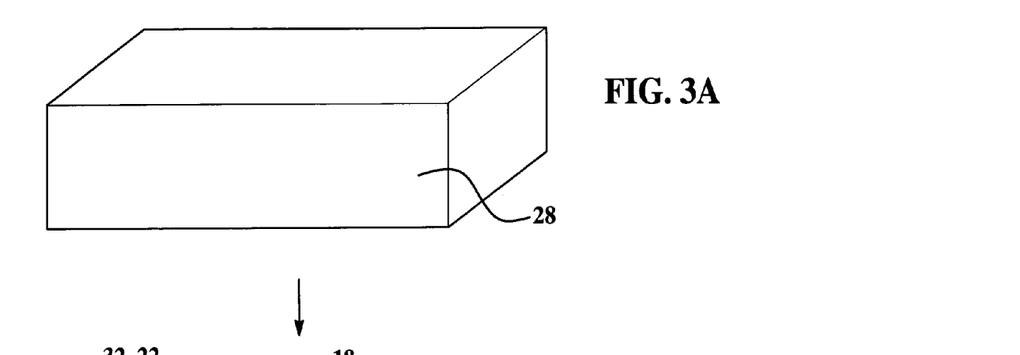
FIGS. 3A through 3C depict semi-schematic perspective views of another embodiment of the method for forming another embodiment of the sensing device.
Figure 3B:
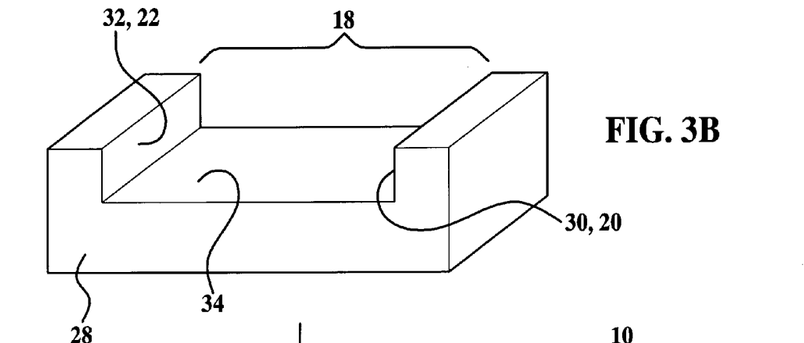
Figure 3C:
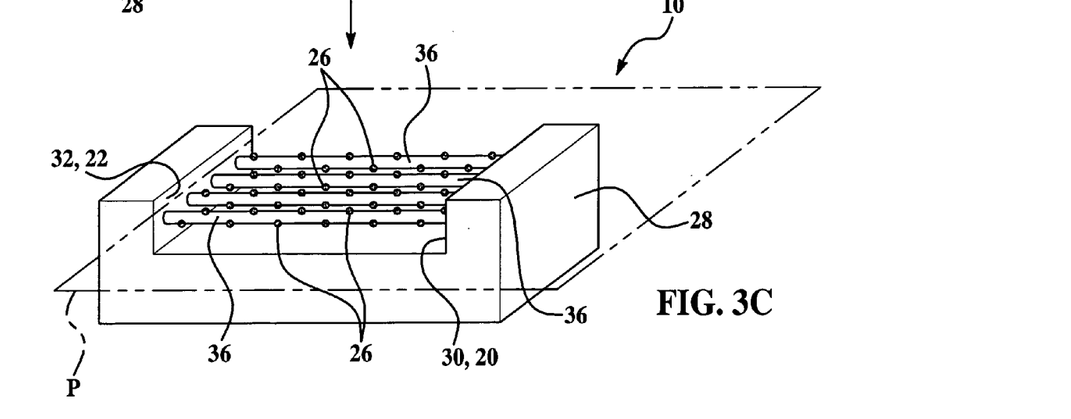

Referring now to FIGS. 3A, 3B and 3C together, another embodiment of the method for forming another embodiment of the sensing device 10' is depicted. Very generally, FIG. 3A depicts a substrate 28, and FIG. 3B depicts the removal of a portion of the substrate 28 to define the optical cavity 18 having at least two opposed cavity sidewalls 30, 32 (which as described further hereinbelow may be, or may have established thereon, reflective surfaces 20, 22) and a cavity bottom 34. FIG. 3C depicts the formation of nanowires 36 in the optical cavity 18. As shown, the nanowires 36 have nanoparticles 26 established thereon.

Specifically referring to FIGS. 3A and 3B together, the substrate 28 may be a single material (e.g., silicon), a mixture of materials, or layers of different materials (e.g., a silicon-on-insulator (SOI) wafer (not shown)). Etching of the substrate 28 may be accomplished via anisotropic wet etching (e.g., with KOH), with directional dry etching (i.e., reactive ion etching), ion milling, and/or other like etching processes. When etching a single material, the depth of the cavity 18 depends, at least in part, on the amount of time during which etching takes place. When etching a silicon-on-insulator wafer, the insulator of the wafer acts as an etch stop. As such, the depth of the cavity 18 depends on the thickness of the silicon layer on the insulator. Other semiconductor-on-insulator structures may also be used. In some instances, a GaAs wafer may be used with appropriate measures taken to smooth sidewalls 30, 32 and grow epitaxial layers of different refractive indices to form the reflecting stack.

As previously described, etching results in the formation of cavity sidewalls 30, 32 and a cavity bottom 34. The cavity sidewalls 30, 32 either form the reflective surfaces 20, 22 of the cavity 18, or they support an additional layer (not shown) formed of reflective material that functions as the reflective surfaces 20, 22. In an embodiment in which the substrate 28 is formed of a desirable reflective material, the sidewalls 30, 32 form the reflective surfaces 20, 22.

In an embodiment in which the substrate 28 is formed of an undesirable material for the reflective surface(s) 20, 22, a layer having a desirable reflectivity may be established on the sidewall(s) 30, 32. Such a layer may be epitaxially grown on the cavity sidewall(s) 30, 32, or it may be deposited by evaporation or other techniques.

Referring now to the embodiment shown in FIG. 3C, the nanowires 36 may be grown laterally or horizontally from one sidewall 30 to another sidewall 32, from one sidewall 32 to another sidewall 30, and/or from both of the sidewalls 30, 32 toward each other to form nanowires 36. In each of these non-limiting examples of growth scenarios, the formed nanowires 36 contact each of the reflective surfaces 20, 22.

Figure 3D:
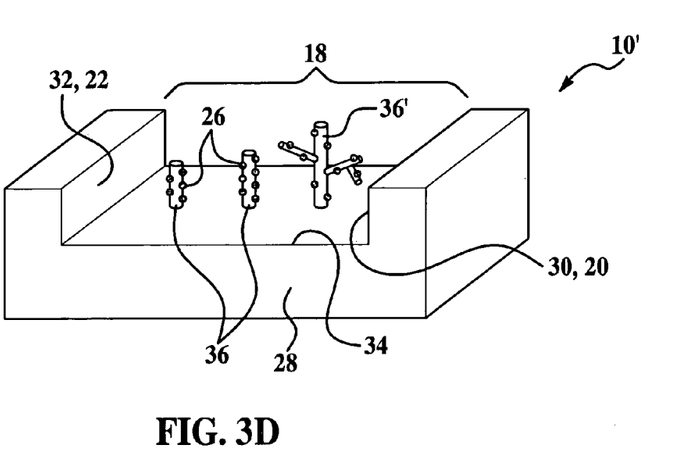
FIG. 3D is a semi-schematic perspective view of an alternate embodiment of the sensing device.
Figure 3E:
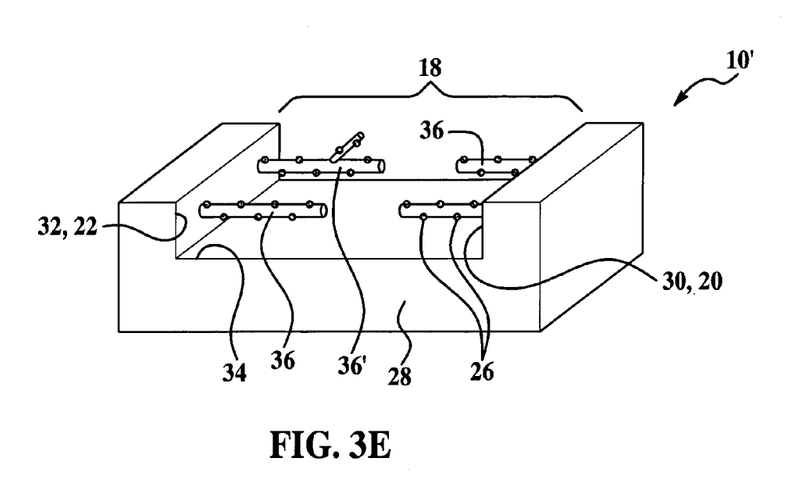
FIG. 3E is a semi-schematic perspective view of yet a further alternate embodiment of the sensing device.

FIGS. 3D and 3E show alternate non-limiting examples of suitable devices 10' according to embodiments of the present disclosure, where nanowires 36, 36' contact a single surface (not necessarily one of the reflective surfaces 20, 22, as demonstrated in FIG. 3D).

FIG. 3D depicts decorated nanowires 36 and a decorated hyper-branched nanowire 36' extending from cavity bottom 34.

FIG. 3E depicts decorated nanowires 36 and branched nanowires 36' extending from a respective reflective surface 20, 22. Although nanowires 36, 36' are shown extending from each of surfaces 20, 22, it is to be understood that nanowires 36, 36' could extend solely from surface 20 or solely from surface 22.

In an embodiment in which the sides 30, 32 of the etched cavity 18 define the reflective surface(s) 20, 22, "contact" means that the nanowire 36, 36' is grown from or attaches to the reflective surface(s) 20, 22. In an embodiment in which one or more additional layers of reflective material define the reflective surface(s) 20, 22, "contact" means that a portion of the nanowire 36, 36' extends through the reflective surface(s) 20, 22, or that nanowire 36, 36' is attached to the one or more additional layers.

As previously stated, it is to be understood that the reflecting surfaces 20, 22 (whether formed integrally with the sides 30, 32 or as an additional layer) are selected so that nanowire growth from the substrate 28 is not substantially inhibited.

In an embodiment, the substrate 28 (or top layer of an SOI substrate) from which the nanowires 36, 36' are grown may be cut or polished with the surface plane being a (110) crystal lattice plane. Such a substrate 28 (or top layer) is referred to as a (110) oriented Si substrate. As used herein, the (110) plane is considered to be horizontally oriented with respect to the Cartesian coordinate system. The (110) oriented substrate 28 (or top layer) further has (111) planes of the Si crystal lattice, at least some of which are approximately perpendicular to, and intersect with, the horizontally oriented (110) surface of the substrate 28 (or top layer). These intersecting (111) planes are referred to herein as vertically oriented (111) planes or surfaces, noting that the (111) planes are approximately vertically oriented relative to the horizontal (110) surface of the substrate 28 (or top layer).

In another embodiment, the cavity bottom 34 may be configured to have the (111) crystal lattice planes, so that nanowires 36, 36' may be grown therefrom. In this embodiment, the (111) plane is considered to be horizontally oriented with respect to the Cartesian coordinate system.

In these embodiments, the term "horizontal" generally refers to a direction or a plane that is parallel with plane P shown in FIG. 3C, while the term "vertical" generally refers to a direction or plane that is substantially or approximately perpendicular to the plane P shown in FIG. 3C.

The (111) surface orientation enables growth of the nanowires 36, 36'; as such, any suitable method may be used to grow the nanowires 36, 36'. In an embodiment, nanowire 36, 36' growth is accomplished by establishing a catalyst on the reflective surface(s) 20, 22, and exposing the catalyst to a precursor gas that initiates growth of the nanowire 36, 36'. A non-limiting example of the formation of nanowires 36, 36' is described in U.S. patent application Ser. No. 10/738,176 filed on Dec. 17, 2003 (U.S. Publication No. 2005/0133476, published on Jun. 23, 2005), incorporated by reference herein in its entirety.

Non-limiting examples of the types of nanowires 36, 36' that may be formed include silicon nanowires, germanium nanowires, compound semiconductor nanowires (including lattice mis-matched nanowires (e.g., indium phosphide nanowires grown on silicon with a lattice mis-match of about 8%)), or the like, or combinations thereof.

As depicted in FIG. 3C, the nanowires 36, 36' include metal nanoparticles 26 established thereon, as discussed above.

In any of the embodiments of nanowires 24, 24', 36, 36' discussed herein, it is to be understood that there may be segments of different material composition along the length of an individual nanowire 24, 24', 36, 36'. The different segments may advantageously be used to position the nanoparticles 26 along the length of a respective nanowire(s) 24, 24', 36, 36', which position may be utilized to maximize signal intensity.

Embodiments of the sensing device 10, 10' have a cavity surface that is substantially parallel to the nanowires 24, 24', 36, 36'. For example, the nanowires 24, 24' may be substantially parallel to the remaining portion of the spacer layer 14 (which defines one side of the optical cavity 18, though it is to be understood that, with the nanowires 24, 24', the recessed surface of the etched layer 14 may not necessarily be vertical), and the nanowires 36, 36' may be substantially parallel to the cavity bottom 34. It is to be understood that generally it is desirable for these portions of the cavity 18 to remain relatively non-reflective when compared to the reflective surfaces 20, 22. As such, a substantially non-reflective spacer layer 14 is selected for the embodiment of the sensing device 10 shown, for example, in FIG. 2C. For the nanowires 36, 36' of the embodiment of the sensing device 10' shown, for example, in FIG. 3C, a layer of suitable index of refraction and thickness may form, or be placed on the bottom surface 34 of the cavity 18 (in an example, this layer would be the insulator of an SOI substrate).

Figure 4:
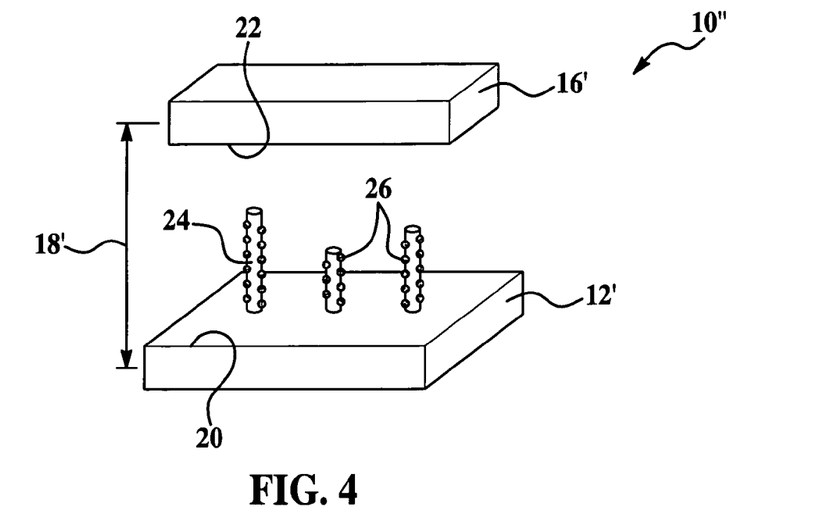
FIG. 4 is a semi-schematic perspective view of another embodiment of the sensing device.

An alternate embodiment of optical cavity 18' of sensing device 10" is shown in FIG. 4. In this embodiment, cavity 18' is not an enclosed cavity. Rather, cavity 18' is formed by opposed, substantially parallel surfaces of an external mirror 16' and reflective substrate 12', and may be a macro-scale cavity 18', e.g., from about 1 mm to about 1 m. It is to be understood that mirror 16' may be formed from any of the materials and by any of the processes described above regarding layer 16, and substrate 12' may be formed from any of the materials and by any of the processes described above regarding substrate 12. It is to be further understood that materials and processes that may not be compatible with the materials and processes used to form the monolithic structures shown in the series of FIGS. 2 and 3 may be used to form the external mirror 16'.

In the embodiments of FIGS. 2A-2F and FIGS. 3A-3E, the optical cavity 18 is micro-scale, e.g., from about 0.1 microns to about 100 microns, and monolithic. As defined herein, "monolithic" means that the cavity is formed within or upon a single substrate.

In any of the cavities 18, 18' described herein, the definition of the cavity spacing may be, but is not necessarily equal to the distance between surfaces 20, 22. An example of when the cavity spacing is not equal to the inter-surface 20, 22 distance is when, for example, the 'mirror' 12, 12', 16, 16', 28 has a physical thickness, as in the case of a distributed Bragg reflector 50 or two coupled, partially transparent surfaces. In this case, the actual cavity spacing or length boundary will be located within the physical thickness of the mirror(s) (12', 16', this cavity spacing 18' being depicted schematically in FIG. 4).

In any of the embodiments herein, the nanowires 24, 24', 36, 36' may be conducting, semiconducting, or insulating. Some non-limiting examples of suitable nanowire materials are elements or compounds from Group IV, Group III-V, or Group II-VI. In an embodiment, the nanowire materials are selected from Si, Ge, SiGe, GaAs, InP, GaN, and combinations thereof.

In the embodiments shown in the various figures, the nanowires 24, 24', 36, 36' are depicted as being substantially vertical or substantially horizontal with respect to one or more surfaces of the cavity 18, 18'. However, it is to be understood that the nanowires 24, 24', 36, 36' may be grown at any suitable angle with respect to one or more of the cavity surfaces and/or with respect to other nanowire(s) 24, 24', 36, 36' within a respective cavity 18, 18'.

Figure 5:
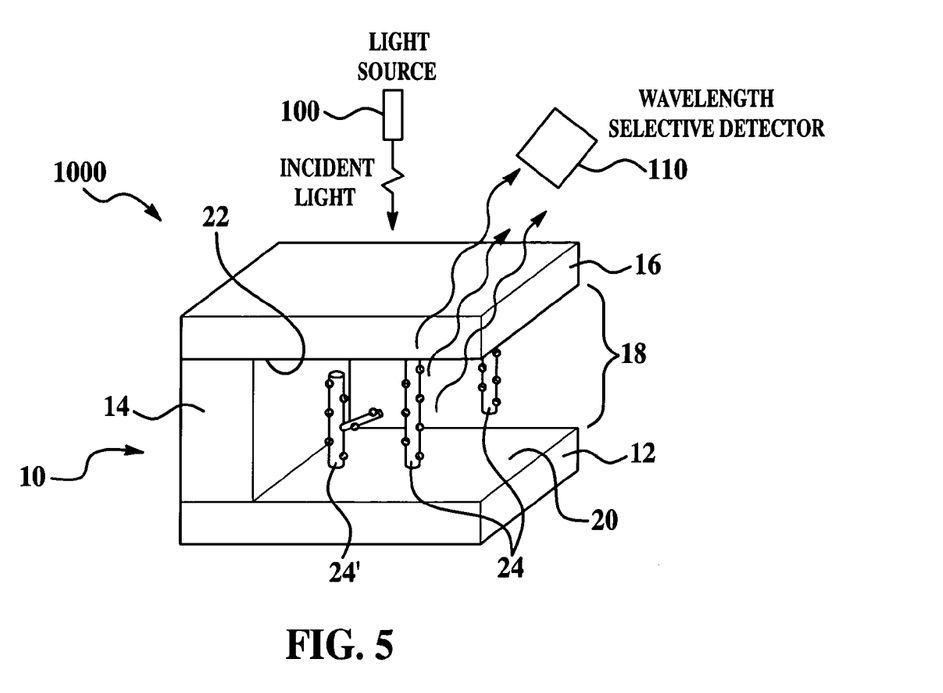
FIG. 5 is a semi-schematic perspective view of a sensing system according to embodiment(s) of the present disclosure.

Referring now to FIG. 5, there is depicted an embodiment of a system 1000 for using an embodiment of the sensing device 10, 10'. A sample containing one or more species (e.g., present as atoms, molecules, ions, chemical and/or biological complexes, etc.) is introduced into the optical cavity 18. Without being bound to any theory, it is believed that the metal nanoparticles 26 present on the nanowires 24, 24', 36, 36' provide locally enhanced electromagnetic fields and thus enhance electromagnetic scattering by any species in proximity to the metal nanoparticles 26. Spectroscopic analysis (e.g. Raman spectroscopy, including surface-enhanced Raman spectroscopy), may be performed by shining a light of a single wavelength (e.g., a laser) from a light source 100 (for example, normal to the cavity 18, as shown) into the cavity 18. In this embodiment, the length of the optical cavity 18 is designed equal to $(n/2)(\lambda_{illumination\ source})$, where n is an integer. The species located at or near the metal nanoparticles 26 scatters the light and shifts the wavelength. The shifts in wavelength may be measured by any suitable wavelength selective detector 110, which is generally not normal to the cavity 18, though it could be normal thereto in some instances, if appropriate and/or desired. The spectrum of wavelength shifts provides a "fingerprint" that is indicative of one or more of the species in the sample that was proximate to the nanowire 24, 24', 36, 36'.

It is to be understood that the light source 100 may be integrated with the device 10, 10', 10", or it may be separate therefrom, but operatively positioned adjacent thereto. Similarly, the wavelength selective detector 110 may be integrated with the device 10, 10', 10", or it may be separate therefrom, but operatively positioned adjacent thereto. Yet further, light source 100 may be integrated with device 10, 10', 10" while detector 110 is separate therefrom; or vice versa.

It is believed that the combination of the metal nanoparticle coated nanowires 24, 26 and the optical cavity 18 advantageously enhances the scattered signal from the one or more species. The optical cavity 18 provides for an enhanced electromagnetic field within the cavity 18 when illuminated by a single wavelength source (e.g. a laser) that is resonant with the cavity 18. It is believed that the electromagnetic field is enhanced on a local, nanometer length scale in proximity to the metal nanoparticles 26. The cavity enhancement and the separate nanoparticle enhancement are expected to combine in a multiplicative or even power-law manner to yield a scattered signal significantly enhanced from either the cavity 18 or the nanoparticles 26 alone. The dimensions and materials selected for the optical cavity 18 tune the optical cavity for a particular wavelength. In an embodiment, the spacing of the reflective surfaces 20, 22 forming the optical cavity 18 is a one half integer multiple of the wavelength of light that is used during spectroscopic analysis (e.g., Surface Enhanced Raman Spectroscopy (SERS)).

Furthermore, the quality factor (i.e., "Q") of the optical cavity 18 may be selected to enhance the overall sensitivity of the sensing device 10, 10'. Generally, the sensitivity of the device 10, 10' may be enhanced by the quality factor or by a square of the quality factor. Altering the dimensions and materials of the cavity 18 alters the quality factor. As such, the quality factor of the optical cavity 18 is tunable so that optimal sensitivity may be achieved. Optimal sensitivity may include detecting as little as a few atoms, molecules, ions, etc. of the species present in the sample. Generally, the optical intensity inside the cavity 18 is enhanced by the quality factor, so a higher Q is generally better. Scattered light will be at a different wavelength than the incident light, and at least in principle, the (high Q) mirrors 20, 22, 50 may be designed to reflect the laser light but pass the scattered light.

Embodiments of the sensing device 10, 10', 10" include, but are not limited to the following advantages. Without being bound to any theory, it is believed that the optical cavity 18 of the sensing device 10, 10', 10" and the metal nanoparticle 26 coated nanowires 24, 24', 36, 36' each advantageously enhances the light and the signal(s) that is/are produced during spectroscopic analysis. The optical cavity 18 may be designed to have a desirable quality ("Q") factor so as to greatly enhance the intensity of the light incident on the species being measured, and therefore the sensitivity of the device 10, 10', 10". The nanoparticles 26 enhance the response to the light incident on the species. Therefore, the combination of the optical cavity 18, 18' and the nanoparticles 26 greatly enhances the sensitivity of the device 10, 10', 10".

While several embodiments have been described in detail, it will be apparent to those skilled in the art that the disclosed embodiments may be modified. Therefore, the foregoing description is to be considered exemplary rather than limiting.

What is claimed is:

1. An optical sensing device, comprising:
    an optical cavity having two substantially opposed reflective surfaces;
    at least one nanowire operatively disposed in the optical cavity; and
    a plurality of metal nanoparticles established on a surface of and along a length of the at least one nanowire;
    wherein each of the plurality of metal nanoparticles is formed of a metal material selected from gold, silver, copper, platinum, palladium, alloys thereof, and combinations thereof, and wherein each of the plurality of metal nanoparticles has a bi-material core-shell structure.

2. The optical sensing device as defined in claim 1 wherein the optical cavity has a third surface, and wherein the at least one nanowire contacts at least one of the three surfaces of the optical cavity.

3. The optical sensing device as defined in claim 1 wherein the at least one nanowire is selected from an unbranched nanowire, a branched nanowire, a hyper-branched nanowire, and combinations thereof.

4. The optical sensing device as defined in claim 1 wherein at least one of the two substantially opposed reflective surfaces is formed integrally with a material that defines a side of the optical cavity.

5. The optical sensing device as defined in claim 1 wherein at least one of the two substantially opposed reflective surfaces is a reflective layer formed of the material of the reflective surfaces established on a material that defines a side of the optical cavity.

6. The optical sensing device as defined in claim 1 wherein the two substantially opposed reflective surfaces are spaced at least a one half integer multiple of a wavelength of light used for Raman spectroscopy.

7. The optical sensing device as defined in claim 1 wherein a shell of the bi-material core-shell structure is selected from silicon oxide, silicon nitride, metal oxides, glass, and combinations thereof.

8. The optical sensing device as defined in claim 1 wherein a core of the bi-material core-shell structure is selected from a first metal material, and wherein a shell of the bi-material core-shell structure is selected from a second metal material, the first metal material being different than the second metal material.

9. The optical sensing device as defined in claim 1 wherein one of the two substantially opposed reflective surfaces is established on a substrate, wherein an other of the two substantially opposed reflective surfaces is established on a second layer, wherein the substrate, the second layer, or combinations thereof include a stack of materials, and wherein the stack of materials includes at least one material having a refractive index different from at least one other material in the stack.

10. The optical sensing device as defined in claim 1 wherein one of the two substantially opposed reflective surfaces is integrally formed with a substrate, and wherein an other of the two substantially opposed reflective surfaces is integrally formed with a second layer opposed to the substrate.

11. The optical sensing device as defined in claim 10, further comprising a spacer layer defining an other surface of the cavity and separating the substrate from the second layer.

12. A sensing system, comprising:
an optical sensing device, including:
an optical cavity having two substantially opposed surfaces;
a reflective layer established on each of the two substantially opposed surfaces of the optical cavity such that surfaces of the respective reflective layers face one another;
at least one nanowire operatively disposed in the optical cavity; and
a plurality of metal nanoparticles established on a surface of and along a length of the at least one nanowire;
wherein each of the plurality of metal nanoparticles is formed of a metal material selected from gold, silver, copper, platinum, palladium, alloys thereof, and combinations thereof, and wherein each of the plurality of metal nanoparticles has a bi-material core-shell structure;
a light source positioned adjacent to the sensing device to operatively transmit light of the predetermined wavelength into the optical cavity; and
a wavelength selective detector operatively positioned adjacent the sensing device.

13. The system as defined in claim 12 wherein the optical cavity has a third surface, and wherein the at least one nanowire contacts at least one of the three surfaces of the optical cavity.

14. The sensing system as defined in claim 12 wherein a spacing of the two substantially opposed reflective surfaces forming the optical cavity is a one half integer multiple of a wavelength of the light.

15. A method for forming an optical sensing device, comprising:
selecting a plurality of metal nanoparticles such that each is formed of a metal material selected from gold, silver, copper, platinum, palladium, alloys thereof, and combinations thereof, and such that each of the plurality of metal nanoparticles has a bi-material core-shell structure;
forming an optical cavity having two substantially opposed reflective surfaces;
operatively disposing at least one nanowire in the optical cavity; and
establishing the plurality of metal nanoparticles on a surface of and along a length of the at least one nanowire.

16. The method as defined in claim 15 wherein forming the optical cavity is accomplished by:
establishing a spacer layer on a substrate;
establishing a second layer on the spacer layer; and
etching away a portion of the spacer layer.

17. The method as defined in claim 16, further comprising establishing a stack of materials as the substrate, the second layer, or combinations thereof, wherein the stack of materials includes at least one material having a refractive index different from at least one other material in the stack.

18. The method as defined in claim 16 wherein etching away a portion of the spacer layer exposes a portion of each of the substrate and the second layer, and wherein the method further comprises establishing a reflective layer on at least one of the exposed portion of the substrate or the exposed portion of the second layer.

19. The method as defined in claim 16 wherein operatively disposing the at least one nanowire is accomplished by growing the nanowire from the substrate to the second layer, from the second layer to the substrate, from each of the substrate and second layer to form respective portions of the at least one nanowire, from the remaining spacer layer, from the substrate, from the second layer, or combinations thereof.

20. The method as defined in claim 16 wherein the substrate and second layer are formed of a material selected for the reflective surfaces, and wherein the substrate and second layer respectively form the two substantially opposed reflective surfaces.

21. The method as defined in claim 15 wherein forming the optical cavity is accomplished by etching away at least a portion of a substrate to define two opposed cavity sidewalls and a cavity bottom within the substrate.

22. The method as defined in claim 21, further comprising growing a material selected for the reflective surfaces on at least one of the two cavity sidewalls, thereby forming at least one of the two substantially opposed reflective surfaces.

23. The method as defined in claim 21 wherein operatively disposing the at least one nanowire is accomplished by growing the nanowire from one of the two opposed cavity sidewalls to an other of the two opposed cavity sidewalls, from each of the opposed cavity sidewalls to form respective portions of the at least one nanowire, from the cavity bottom, from one of the two opposed cavity sidewalls, or combinations thereof.

24. A method for detecting a species, comprising:
introducing a sample to an optical cavity of an optical sensor, the optical sensor including:
the optical cavity having two substantially opposed reflective surfaces;
at least one nanowire operatively disposed within the optical cavity; and
a plurality of metal nanoparticles established on a surface of and along a length of the at least one nanowire;
wherein each of the plurality of metal nanoparticles is formed of a metal material selected from gold, silver, copper, platinum, palladium, alloys thereof, and combinations thereof, and wherein each of the plurality of metal nanoparticles has a bi-material core-shell structure;
exposing the sensor to light of the predetermined wavelength, whereby at least one species within the sample and proximate to the at least one nanowire scatters the light and shifts the predetermined wavelength; and
identifying the at least one species through analyses of the wavelength shifts.

* * * * *